United States Patent
Liu

(10) Patent No.: US 9,427,024 B2
(45) Date of Patent: Aug. 30, 2016

(54) ELECTRONIC CIGARETTE CASING AND ELECTRONIC CIGARETTE DEVICE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

(*) Notice: Subject to any disclaimer, the term of this patent is extended or adjusted under 35 U.S.C. 154(b) by 663 days.

(21) Appl. No.: 13/818,684

(22) PCT Filed: Sep. 21, 2012

(86) PCT No.: PCT/CN2012/081736
§ 371 (c)(1),
(2) Date: Feb. 24, 2013

(87) PCT Pub. No.: WO2014/043887
PCT Pub. Date: Mar. 27, 2014

(65) Prior Publication Data
US 2014/0083443 A1 Mar. 27, 2014

(51) Int. Cl.
*A24F 47/00* (2006.01)
*A61M 15/06* (2006.01)
*H02J 7/34* (2006.01)
*H02J 7/00* (2006.01)
*A24F 15/12* (2006.01)

(52) U.S. Cl.
CPC ............ *A24F 47/008* (2013.01); *A24F 47/00* (2013.01); *A61M 15/06* (2013.01); *H02J 7/0042* (2013.01); *H02J 7/0044* (2013.01); *H02J 7/0054* (2013.01); *A24F 15/12* (2013.01); *H02J 7/345* (2013.01)

(58) Field of Classification Search
CPC .... A24F 47/00; A24F 47/002; A24F 47/006; A24F 47/008; A61M 15/06; H02J 7/0054; H02J 7/345
See application file for complete search history.

(56) References Cited

U.S. PATENT DOCUMENTS

2007/0229025 A1* 10/2007 Tsai et al. ............... 320/111
2012/0227753 A1* 9/2012 Newton ............... 131/347
2012/0319471 A1* 12/2012 Miller ............... 307/9.1

FOREIGN PATENT DOCUMENTS

CN 201571500 U * 9/2010

* cited by examiner

*Primary Examiner* — Anthony Calandra
(74) *Attorney, Agent, or Firm* — Cheng-Ju Chiang

(57) ABSTRACT

The invention provides an electronic cigarette casing and an electronic cigarette device, the electronic cigarette casing comprises a case body for accommodating electronic cigarettes, a first power supply configured in the case body and a charging control system for controlling the first power supply to charge the electronic cigarettes, the first power supply comprises a farad capacitor. The electronic cigarette casing using the farad capacitor instead of the traditional batteries to supply electrical power, can achieve the technical effects of safe and reliable charging/discharging, rapid charging, and more charging and discharging times.

11 Claims, 3 Drawing Sheets

ELECTRONIC CIGARETTE CASING AND ELECTRONIC CIGARETTE DEVICE

CROSS REFERENCE TO RELATED APPLICATIONS

The present application is a 35 U.S.C. §371 National Phase conversion of International (PCT) Patent Application No. PCT/CN2012/081736, filed on Sep. 21, 2012, the disclosure of which is incorporated by reference herein. The PCT International Patent Application was filed in Chinese.

TECHNICAL FIELD

This invention relates to an electronic cigarette technology, and particularly to an electronic cigarette casing and an electronic cigarette device.

DESCRIPTION OF BACKGROUND

Electronic cigarettes are a kind of simulating cigarettes which heat and atomize materials having flavors through heating wire to generate smoke for user's suction, the electronic cigarettes are usually placed within the electronic cigarette casing, the electronic cigarettes generally comprises detachable sucking rod and power rod, and the electronic cigarette casings commonly use a rechargeable battery to store energy and charge the electronic cigarettes. During charging the power rod is inserted into the charging socket inside of the electronic cigarette casing in order to be connected with and charged by the rechargeable battery in the electronic cigarette casing.

However, the electronic cigarette casing with rechargeable battery has the defects of less charging and discharging times, being unsafe (ease to fire and explode), long charging time, small charging current and so on.

SUMMARY

An object of the present invention is to provide an electronic cigarette casing, which is safe and reliable to charge and discharge, and rapidly charged, and has more charging and discharging times.

To achieve the above object, the present invention provides an electronic cigarette casing, comprising a case body for accommodating electronic cigarettes, a first power supply configured in the case body and a charging control system for controlling the first power supply to charge the electronic cigarettes, the first power supply comprises a farad capacitor.

Furthermore, the charging control system further comprises: a charging socket built in the electronic cigarette casing; a switch module built in electronic cigarette casing, and generating a triggering signal when an electronic cigarette is connected to the charging socket; and a first charging control module connected to the charging socket, the switch module and the first farad capacitor, and conducting the first farad capacitor with the electronic cigarette.

Furthermore, the first power supply further comprises a first rechargeable battery built in the electronic cigarette casing and connected to the first charging control module for charging the electronic cigarettes or the first farad capacitor.

Furthermore, the charging control system further comprises: a storage module connected to the first charging control module, and storing a predetermined state parameter, a first charging parameter and a second charging parameter; and a state detecting module connected to the first charging control module and the storage module, and judging the current charging state is a first state or a second state according to the predetermined state parameter;

wherein, the first charging control module conducts the first farad capacitor with the electronic cigarette and selects the first charging parameter to charge in the first state, and keeps the first farad capacitor conducted with the electronic cigarette or conducts the first rechargeable battery with the electronic cigarette and selects the second charging parameter to charge.

Furthermore, the charging control system further comprises a second charging control module connected to the first farad capacitor, the first rechargeable battery and the switch module, and conducting the first rechargeable battery with the first farad capacitor when the switch module does not generate the triggering signal.

Furthermore, the first charging control module, the storage module, the state detecting module and the second charging control module are integrated on one integrated circuit.

Furthermore, the charging control system further comprises a state indicating module configured on an outer surface of the case body and connected to the integrated circuit, for indicating the work state of the electronic cigarette casing.

Furthermore, the electronic cigarette casing further comprises a bracket module and a PCB board located in the case body, and the bracket module comprises a sucking rod tray, a sucking rod frame and a base support; wherein, the sucking rod tray works in coordination with the sucking rod frame to accommodate the sucking rods of the electronic cigarettes; the integrated circuit is configured on the PCB board, and the PCB board is fixed to the base support.

Furthermore, the first farad capacitor and the first rechargeable battery are fixed on the base support and electrically connected to the PCB board.

Furthermore, the PCB board is configured with a charging port thereon for connecting with an outer power supply to charge the first farad capacitor and the first rechargeable battery.

Furthermore, the case body comprises a base box and a box cover movably connected to the base box.

Additionally, the present invention further provides an electronic cigarette device, the electronic cigarette device comprises the electronic cigarette casing described above, and electronic cigarettes accommodated in the electronic cigarette casing.

Furthermore, the electronic cigarettes each comprises mutually connected sucking rod and power rod, and the sucking rod is configured with atomizers therein, and the power rod is configured with a second power supply therein for energizing the atomizers, and the second power supply at least comprises any one of a second farad capacitor and a second rechargeable battery.

The beneficial effects of the electronic cigarette casing and the electronic cigarette device are that: the technical solution using the farad capacitor instead of the traditional batteries to supply electrical power, can achieve the technical effects of safe and reliable charging/discharging, rapid charging, and more charging and discharging times.

DETAILED DESCRIPTION OF THE EMBODIMENTS

It should be noted that, the embodiments and the characteristics in the embodiments can be mutually combined in case of no confliction; the present invention will be described in further detail below through the embodiments in conjunction with the accompanying drawings.

Figure 1:
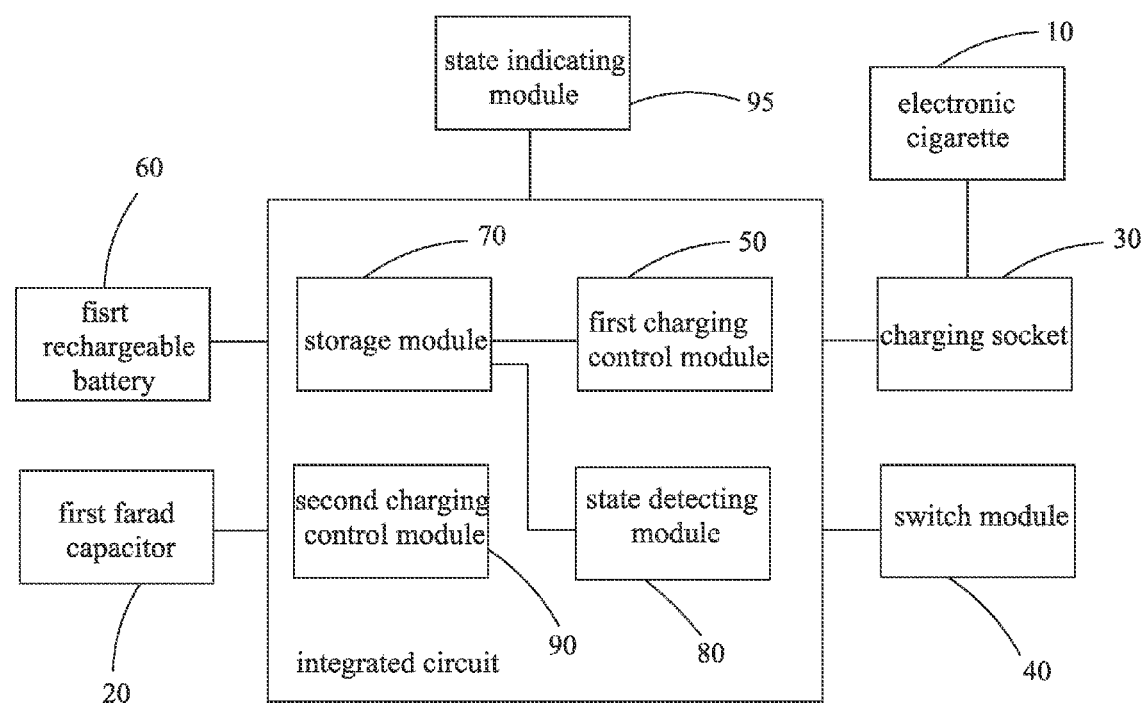
FIG. 1 is a circuit block diagram of an electronic cigarette casing in accordance with an embodiment of the present invention.
Figure 2:
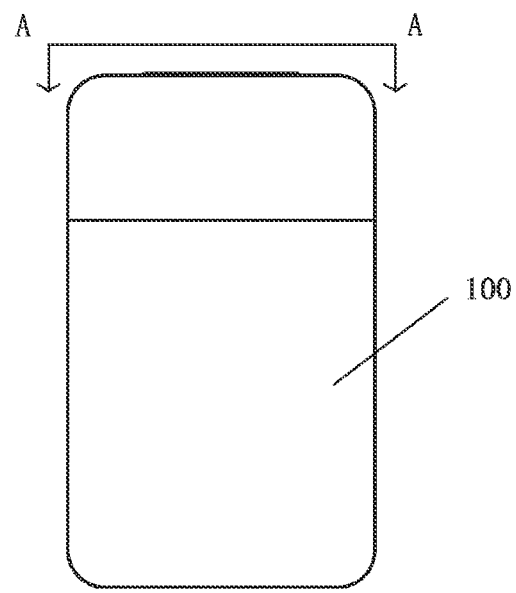
FIG. 2 is a side view of the electronic cigarette casing in accordance with the embodiment of the present invention.
Figure 3:
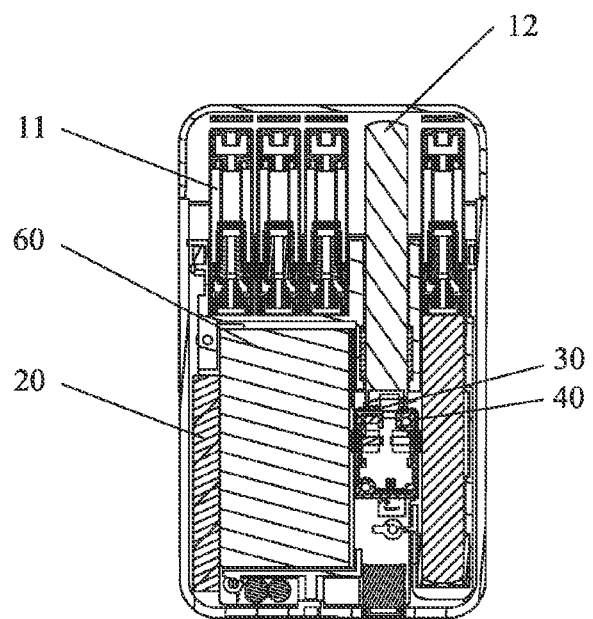
FIG. 3 is a cross-sectional view of the electronic cigarette casing shown in FIG. 2, taken along A-A line.
Figure 4:
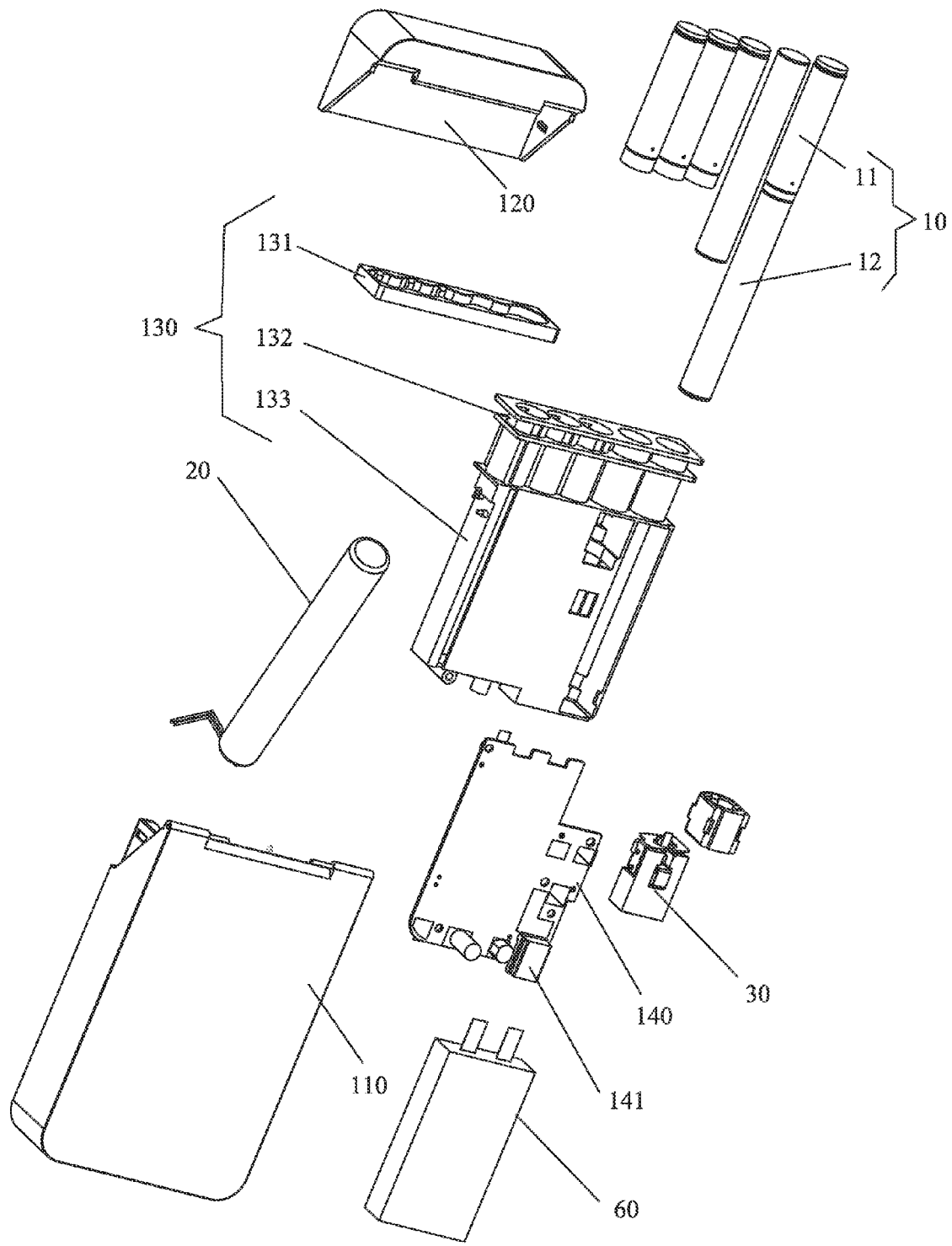
FIG. 4 is an exploded view of the electronic cigarette casing shown in FIG. 2.

As shown from FIG. 1 to FIG. 4, an electronic cigarette casing and an electronic cigarette device are provided according to the embodiments of the present invention. The electronic cigarette casing comprises a case body 100 for accommodating electronic cigarettes, a first power supply disposed in the case body 100, and a charging control system for controlling the first power supply to charge the electronic cigarettes. The first power supply comprises a first Farad capacitor 20. The electronic cigarette device comprises the electronic cigarette casing and electronic cigarettes 10 accommodated in the electronic cigarette casing.

The case body 100 has a rectangular parallelepiped shape, and comprises a base box 110 and a box cover 120 movably connected to the base box 110.

The first farad capacitor 20 is for providing the charging power supply to the electronic cigarettes 10. Specifically, it has the following advantageous effects to use the farad capacitor instead of the traditional rechargeable batteries or disposable batteries for charging the electronic cigarettes 10:

(1) Compared to 2-3 hours' charging time of the rechargeable batteries, the charging time of the farad capacitor charging is short, and only 1 second to 30 seconds;

(2) Compared to the complex protection circuit required by the rechargeable batteries, the farad capacitor does not need the charging circuit like the rechargeable battery, and has simple charging and discharging circuits, high safety factor, and can be used for a long time without maintenance;

(3) compared to that the service life of the rechargeable batteries is less than 500 times, the farad capacitor has long the cycle life, and its cycle times of deep charging and discharging can be up to 10,000 to 500,000 times, and has no "memory effect";

(4) Compared to that the capacity will be gradually decreased after repeatedly charging and discharging the rechargeable batteries, the capacity of the farad capacitor is stable and not changed after repeatedly charging and discharging;

(5) Compared to that electrically energized production of the conventional batteries is easy to cause a short circuit, and cause the battery to fire, explosion, etc., the farad capacitor of the electronic cigarette casing is not electrically energized during production, which would not cause the production accidents of short circuit and explosion and so on, it is safe and reliable;

(6) Compared to the heavier weight of the conventional batteries, the electronic cigarette casing with the farad capacitor becomes lighter;

(7) Compared to the pollution of the discarded conventional batteries to the environment, the farad capacitor is of green environmental protection;

(8) Compared to that the large volume of the conventional batteries, squeezes the limited accommodating space of the electronic cigarette casing, the farad capacitor having a small size, can save the valuable internal space of the electronic cigarette casing for other components.

The charging control system further comprises a charging socket 30, a switch module 40 and a first charging control module 50.

The charging socket 30 is built in the electronic cigarette casing, for connecting with the electronic cigarettes 10 to charge them.

The switch module 40 is also built in the electronic cigarette casing, for generating a triggering signal when an electronic cigarette 10 is connected to the charging socket 30. Specifically, the switch module 40 is configured on the charging socket 30, and is exemplarily a micro-switch, photoelectric switch or proximity sensor.

The first charging control module 50 is connected with the charging socket 30, the switch module 40 and the first farad capacitor 20, and conducts the first farad capacitor 20 with the electronic cigarette 10 for charging according to the triggering signal.

As an embodiment, the first power supply further comprises a first rechargeable battery 60, a storage module 70 and a state detecting module 80.

The first rechargeable battery 60 is built in the electronic cigarette casing, and the first charging control module 50 is further for conducting the first rechargeable battery 60 with the electronic cigarette 10, and the detailed working process is referenced in the hereafter description.

The storage module 70 is connected to the first charging control module 50, and stores a predetermined state parameter, a first charging parameter and a second charging parameter.

The state detecting module 80 is connected to the first charging control module 50 and the storage module 70, for judging the current charging state is a first state or a second state according to the predetermined state parameter. As an embodiment, the rated voltage of the power supply in the electronic cigarette 10 is 3V, and the predetermined state parameter in the storage module 70 is a voltage value of 2.8V corresponded with the power supply in the electronic cigarette, if the state detecting module 80 judges that the current voltage is less than 2.8V, it is determined as a non-full charged state (the first state), otherwise it is determined as a full charged state (the second state) by the state detecting module 80; the first charging parameter represents that the rapid charge current is 100 mA in the first state, and the second charging parameter represents that trickle charge current is 20 mA in the second state. Specifically, the state detecting module 80 determines that it is in the first state (i.e., the voltage value of the power supply in the electronic cigarette is less than 2.8V), the first charging control module 50 conducts the first farad capacitor 20 with the electronic cigarette 10 and selects the first charging parameter (100 mA) to rapid charge; the status detecting module 80 determines that it is in the second state (i.e., the voltage value of the power supply in the electronic cigarette is greater than or equal to 2.8V), the first charging control module 50 keeps the first farad capacitor 20 conducted with the electronic cigarette 10 or conducts the first rechargeable battery 60 with the electronic cigarette 10, and selects the second charging parameter (20 mA) to trickle charge. Thus, the electronic cigarette in the present invention combines the rapid charging manner and the trickle charging manner, to on the one hand ensure fast and convenient charging to the electronic cigarette, on the other hand keep the electronic cigarette connected to the charging socket 30 to maintain it in a full charged state.

The charging control system further comprises a second charging control module 90 and a state indicating module 95. The second charging control module 90 is connected to the first farad capacitor 20, the first rechargeable battery 60 and the switch module 40, for conducting the first rechargeable battery 60 and the first farad capacitor 20 to charge the first farad capacitor 20 by the first rechargeable battery 60 when on electronic cigarette is connected to the charging socket 30 and the switch module 40 does not generate the triggering signal. Therefore, during the empty slot in charging the electronic cigarette 10, the first rechargeable battery 60 charges the first farad capacitor 20, to overcome the defect of the farad capacitor of relatively small capacity. The first charging control module 50, the storage module 70, the state detecting module 80 and the second charging control module 90 are integrated on one integrated circuit (IC).

The state indicating module 95 is configured on an outer surface of the case body 100 and connected to the IC, for indicating the work state of the electronic cigarette casing. The state indicating module 95 comprises one or more LEDs.

The electronic cigarette casing further comprises a bracket module 130 and a PCB board 140 located in the case body 100, and the bracket module 130 comprises a sucking rod tray 131, a sucking rod frame 132 and a base support 133. Specifically, each electronic cigarette 10 comprises mutually connected sucking rod 11 and power rod 12, and the sucking rod 11 is configured with atomizers therein, and the power rod 12 is configured with a second power supply therein for energizing the atomizers. The second power supply at least comprises any one of a second farad capacitor and a second rechargeable battery, the sucking rod tray 131 works in coordination with the sucking rod frame 132 to accommodate the sucking rods 11 of the electronic cigarettes 10; the IC is configured on the PCB board 140, and the first farad capacitor 20 and the first rechargeable battery 60 are fixed on the base support 133 and electrically connected to the PCB board 140, the PCB board 140 is fixed to the base support 133, and the PCB board 140 is configured with a charging port 141 thereon for connecting with an outer power supply to charge the first farad capacitor 20 and the first rechargeable battery 60. The charging port 141 exemplarily is a Mini USB port. The PCB board 140 is further configured with a current limiting circuit connected to the charging port 141 for limiting the charging current, in order to avoid excessive external charging current to damage the first power supply.

The above-mentioned is only the embodiments of the present invention. It should be noted, for the persons of ordinary skill in this field, improvements and modifications within the spirit of the present invention can be made, and the improvements and modifications should be seemed to be included in the claimed scope of this invention.

What is claimed is:

1. An electronic cigarette casing, comprising a case body for accommodating an electronic cigarette, a first power supply configured in the case body and a charging control system for controlling the first power supply to charge a power supply of the electronic cigarette, wherein the first power supply comprises a capacitor;

the capacitor is capable of charging the electronic cigarette instead of traditional rechargeable batteries or disposable batteries;

the capacitor is capable of combining a rapid charging manner and a trickle charging manner to charge the electronic cigarette in the case body, whereby to ensure fast and convenient charging to the electronic cigarette and keep the electronic cigarette in a full charged state;

the charging control system further comprises: a charging socket built in the electronic cigarette casing; a switch module built in electronic cigarette casing, and generating a triggering signal when an electronic cigarette is connected to the charging socket and a first charging control module connected to the charging socket, the switch module and the first capacitor, and conducting the first capacitor with the electronic cigarette;

the first power supply further comprises a first rechargeable battery built in the electronic cigarette casing and connected to the first charging control module for charging the electronic cigarette or the first capacitor;

the charging control system further comprises: a storage module connected to the first charging control module, and storing a predetermined state parameter, a first charging parameter and a second charging parameter; and a state detecting module connected to the first charging control module and the storage module, and judging the current charging state is a first state or a second state according to the predetermined state parameter;

the first charging control module conducts the first capacitor with the electronic cigarette and selects the first charging parameter to charge in the rapid charging manner at the first state, and keeps the first capacitor conducted with the electronic cigarette or conducts the first rechargeable battery with the electronic cigarette and selects the second charging parameter to charge in the trickle charging manner;

the first state is a non-full charged state of the electronic cigarette's power supply; the second state is a full charged state of the electronic cigarette's power supply;

the charging control system further comprises a second charging control module connected to the first capacitor, the first rechargeable battery and the switch module; and the second charging control module is capable of conducting the first rechargeable battery to charge the first capacitor when the switch module does not generate the triggering signal or an electronic cigarette is connected to the charging socket; the first rechargeable battery is capable of charging the first capacitor when no electronic cigarette is present to be charged in the case body, whereby the first rechargeable battery overcomes the relatively small capacity of the capacitor; and the first charging control module, the storage module, the state detecting module and the second charging control module are integrated on one integrated circuit.

2. An electronic cigarette casing, comprising a case body for accommodating electronic cigarettes, a first power supply configured in the case body and a charging control system for controlling the first power supply to charge the electronic cigarettes, wherein the first power supply comprises a capacitor;

the charging control system further comprises: a charging socket built in the electronic cigarette casing; a switch module built in electronic cigarette casing, and generating a triggering signal when an electronic cigarette is connected to the charging socket; and a first charging control module connected to the charging socket, the switch module and the first capacitor, and conducting the first capacitor with the electronic cigarette;

the first power supply further comprises a first rechargeable battery built in the electronic cigarette casing and connected to the first charging control module for charging the electronic cigarettes or the first capacitor;

the charging control system further comprises: a storage module connected to the first charging control module, and storing a predetermined state parameter, a first charging parameter and a second charging parameter; and a state detecting module connected to the first charging control module and the storage module, and judging the current charging state is a first state or a second state according to the predetermined state parameter; wherein the first charging control module conducts the first capacitor with the electronic cigarette and selects the first charging parameter to charge in the first state, and keeps the first capacitor conducted with the electronic cigarette or conducts the first rechargeable battery with the electronic cigarette and selects the second charging parameter to charge;

the charging control system further comprises a second charging control module connected to the first capacitor, the first rechargeable battery and the switch module, and conducting the first rechargeable battery with the first capacitor when the switch module does not generate the triggering signal;

wherein the first charging control module, the storage module, the state detecting module and the second charging control module are integrated on one integrated circuit.

3. The electronic cigarette casing as described in claim 2, wherein the charging control system further comprises a state indicating module configured on an outer surface of the case body and connected to the integrated circuit, for indicating the work state of the electronic cigarette casing.

4. The electronic cigarette casing as described in claim 2, wherein the electronic cigarette casing further comprises a bracket module and a PCB (Printed Circuit Board) board located in the case body, and the bracket module comprises a sucking rod tray, a sucking rod frame and a base support; wherein, the sucking rod tray works in coordination with the sucking rod frame to accommodate a sucking rod of the electronic cigarette; the integrated circuit is configured on the PCB board, and the PCB board is fixed to the base support.

5. The electronic cigarette casing as described in claim 4, wherein the first capacitor and the first rechargeable battery are fixed on the base support and electrically connected to the PCB board.

6. The electronic cigarette casing as described in claim 4, wherein the PCB board is configured with a charging port thereon for connecting with an outer power supply to charge the first capacitor and the first rechargeable battery.

7. The electronic cigarette casing as described in claim 1, wherein the case body comprises a base box and a box cover movably connected to the base box; a rated voltage of the power supply in the electronic cigarette is about 3 V, and the predetermined state parameter in the storage module is a voltage value of about 2.8 V corresponded with the power supply in the electronic cigarette; the first state is that a current voltage of the power supply in the electronic cigarette is less than 2.8 V, and the second state is that the current voltage of the power supply in the electronic cigarette is greater than or equal to 2.8 V; the first charging parameter represents that a rapid charge current is 100 mA in the first state, and the second charging parameter represents that a trickle charge current is 20 mA in the second state.

8. An electronic cigarette device, wherein the electronic cigarette device comprises: an electronic cigarette casing comprising a case body for accommodating electronic cigarettes, a first power supply configured in the case body and a charging control system for controlling the first power supply to charge the electronic cigarettes, wherein the first power supply comprises a capacitor; and electronic cigarettes accommodated in the electronic cigarette casing;

the charging control system further comprises: a charging socket built in the electronic cigarette casing; a switch module built in electronic cigarette casing, and generating a triggering signal when an electronic cigarette is connected to the charging socket; and a first charging control module connected to the charging socket, the switch module and the first capacitor, and conducting the first capacitor with the electronic cigarette;

the first power supply further comprises a first rechargeable battery built in the electronic cigarette casing and connected to the first charging control module for charging the electronic cigarettes or the first capacitor;

the charging control system further comprises: a storage module connected to the first charging control module, and storing a predetermined state parameter, a first charging parameter and a second charging parameter; and a state detecting module connected to the first charging control module and the storage module, and judging the current charging state is a first state or a second state according to the predetermined state parameter; wherein, the first charging control module conducts the first capacitor with the electronic cigarette and selects the first charging parameter to charge in the first state, and keeps the first capacitor conducted with the electronic cigarette or conducts the first rechargeable battery with the electronic cigarette and selects the second charging parameter to charge;

the charging control system further comprises a second charging control module connected to the first capacitor, the first rechargeable battery and the switch module, and conducting the first rechargeable battery with the first capacitor when the switch module does not generate the triggering signal;

the first charging control module, the storage module, the state detecting module and the second charging control module are integrated on one integrated circuit.

9. The electronic cigarette device as described in claim 8, wherein the electronic cigarettes each comprises mutually connected sucking rod and power rod, and the sucking rod is configured with atomizers therein, and the power rod is configured with a second power supply therein for energizing the atomizers, and the second power supply at least comprises any one of a second capacitor and a second rechargeable battery.

10. The electronic cigarette device as described in claim 8, wherein the charging control system further comprises a state indicating module configured on an outer surface of the case body and connected to the integrated circuit, for indicating the work state of the electronic cigarette casing.

11. The electronic cigarette device as described in claim 8, wherein the electronic cigarette casing further comprises a bracket module and a PCB (Printed Circuit Board) board located in the case body, and the bracket module comprises a sucking rod tray, a sucking rod frame and a base support; wherein, the sucking rod tray works in coordination with the sucking rod frame to accommodate the sucking rods of the electronic cigarettes; the integrated circuit is configured on the PCB board, and the PCB board is fixed to the base support.

<p style="text-align:center">* * * * *</p>